United States Patent
Awtrey et al.

(10) Patent No.: US 12,201,326 B2
(45) Date of Patent: *Jan. 21, 2025

(54) KNOTLESS SYNDESMOSIS SYSTEM

(71) Applicant: Wright Medical Technology, Inc., Memphis, TN (US)

(72) Inventors: George Matthew Awtrey, Bartlett, TN (US); Jon Pope Moseley, Arlington, TN (US); Samuel W. Apicelli, Bryn Mawr, PA (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 365 days.

This patent is subject to a terminal disclaimer.

(21) Appl. No.: 17/457,132

(22) Filed: Dec. 1, 2021

(65) Prior Publication Data

US 2022/0079627 A1    Mar. 17, 2022

Related U.S. Application Data

(63) Continuation of application No. 16/333,634, filed as application No. PCT/US2016/066902 on Dec. 15, 2016, now Pat. No. 11,229,456.

(51) Int. Cl.
*A61B 17/04* (2006.01)
*A61B 17/68* (2006.01)
(Continued)

(52) U.S. Cl.
CPC ........ *A61B 17/683* (2013.01); *A61B 17/0401* (2013.01); *A61B 17/0487* (2013.01);
(Continued)

(58) Field of Classification Search
CPC .. A61B 17/0401; A61B 17/683; A61B 17/842
See application file for complete search history.

(56) References Cited

U.S. PATENT DOCUMENTS 5,383,905 A    1/1995   Golds et al.
5,409,499 A    4/1995   Yi
(Continued)

FOREIGN PATENT DOCUMENTS

EP    1013229 A2    6/2000

OTHER PUBLICATIONS

International Search Report and Written Opinion issued in corresponding International Patent Application No. PCT/US2016/066902, Aug. 22, 2017, 14 pages.
(Continued)

*Primary Examiner* — Nicholas W Woodall
(74) *Attorney, Agent, or Firm* — DUANE MORRIS LLP

(57) ABSTRACT

A bone anchor includes a flexible strand defining a first adjustable loop and a friction knot coupled to a proximal end of the first adjustable loop. The friction knot is configured to allow adjustment of the first adjustable loop in a first configuration and is configured to prevent adjustment of the first adjustable loop in a second configuration. A knot capsule includes a body defining an internal knot cavity. The friction knot and a portion of the first adjustable loop are positioned within the internal knot cavity. The internal knot cavity defines one or more impingement surfaces configured to maintain the friction knot in a fixed position within the internal knot cavity when the friction knot is in the second configuration.

30 Claims, 16 Drawing Sheets

(51) Int. Cl.
*A61B 17/84* (2006.01)
*A61B 17/80* (2006.01)

(52) U.S. Cl.
CPC .... *A61B 17/842* (2013.01); *A61B 2017/0409* (2013.01); *A61B 2017/0417* (2013.01); *A61B 2017/0419* (2013.01); *A61B 2017/0445* (2013.01); *A61B 2017/0477* (2013.01); *A61B 2017/0496* (2013.01); *A61B 17/8061* (2013.01)

(56) References Cited

U.S. PATENT DOCUMENTS

| | | | |
|---|---|---|---|
| 5,571,175 | A | 11/1996 | Vanney et al. |
| 5,843,178 | A | 12/1998 | Vanney et al. |
| 6,306,159 | B1 | 10/2001 | Schwartz et al. |
| 7,442,202 | B2 | 10/2008 | Dreyfuss |
| 8,062,334 | B2 | 11/2011 | Green et al. |
| 8,317,825 | B2 | 11/2012 | Stone |
| 8,545,535 | B2 | 10/2013 | Hirotsuka et al. |
| 9,706,985 | B2 * | 7/2017 | Allen ................. A61B 17/0487 |
| 10,779,868 | B2 * | 9/2020 | O'Connor ............ A61B 17/842 |
| 11,529,134 | B2 * | 12/2022 | Taylor ................ A61B 17/0401 |
| 2003/0236555 | A1 | 12/2003 | Thornes |
| 2005/0033363 | A1 | 2/2005 | Bojarski et al. |
| 2007/0203506 | A1 * | 8/2007 | Sibbitt ............... A61B 17/0057 606/139 |
| 2012/0123474 | A1 | 5/2012 | Zajac et al. |
| 2013/0030480 | A1 * | 1/2013 | Donate .............. A61B 17/0401 606/328 |
| 2013/0053897 | A1 | 2/2013 | Brown et al. |
| 2013/0123841 | A1 | 5/2013 | Lyon |
| 2013/0172944 | A1 | 7/2013 | Fritzinger et al. |
| 2014/0011435 | A1 | 1/2014 | Kaneko |
| 2016/0003003 | A1 | 1/2016 | Getzlaf et al. |
| 2016/0038267 | A1 | 2/2016 | Allen et al. |
| 2020/0038010 | A1 * | 2/2020 | Zakhary ............ A61B 17/0401 |
| 2021/0128138 | A1 * | 5/2021 | Bettenga ............... A61F 2/0811 |

OTHER PUBLICATIONS

First Office Action issued in connection with corresponding Canadian Patent Application No. 3,036,800, Mar. 4, 2020 4 pages.
First Examination Report issued in connection with corresponding Australian Patent Application No. 2016432176, May 27, 2019, 3 pages.

* cited by examiner

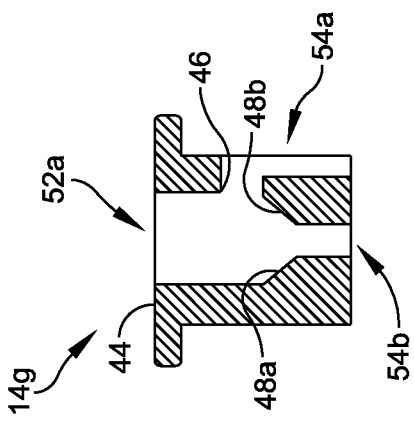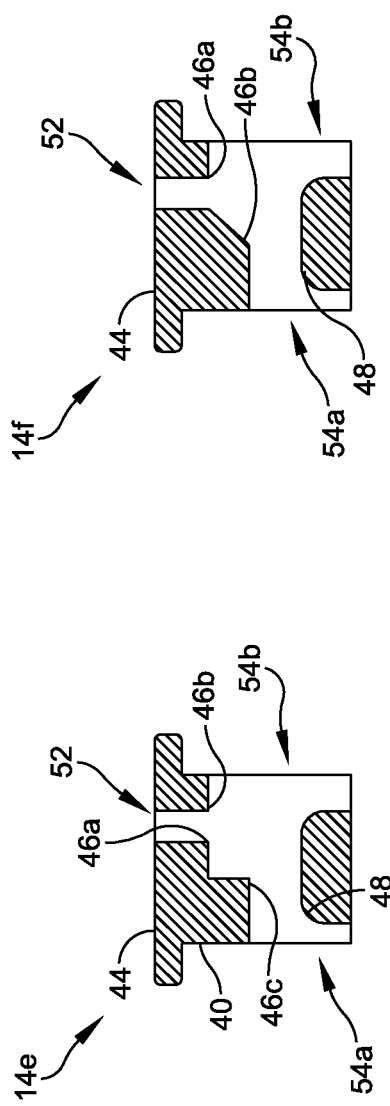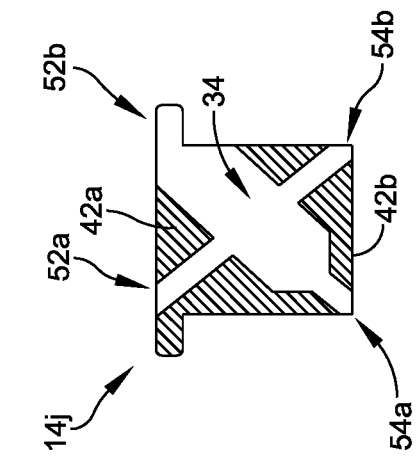

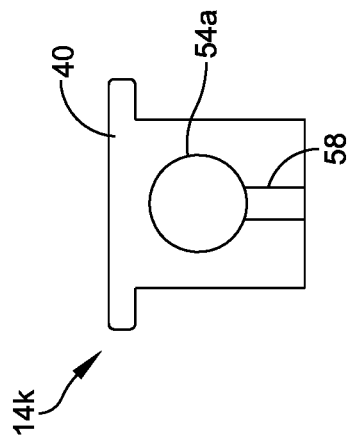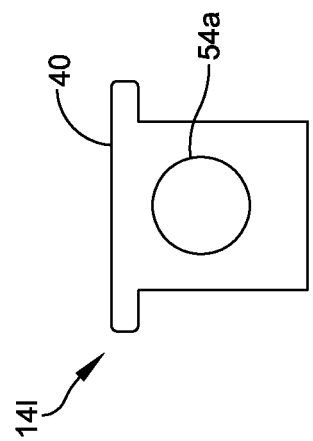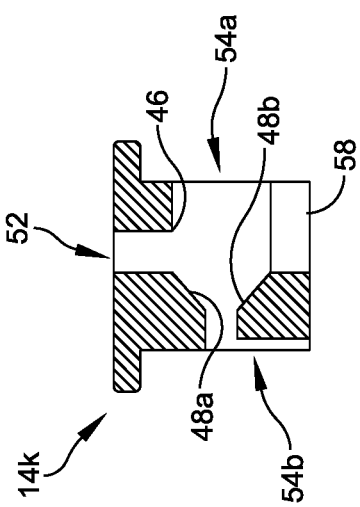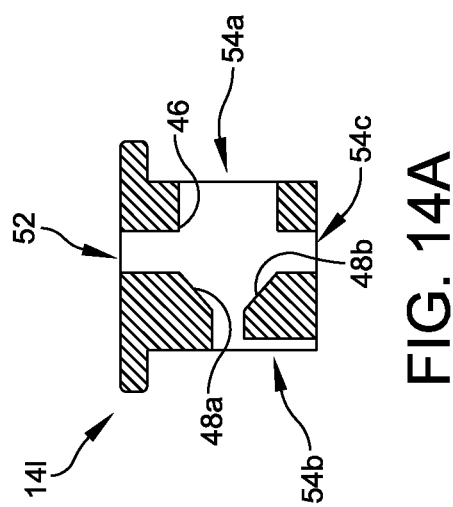

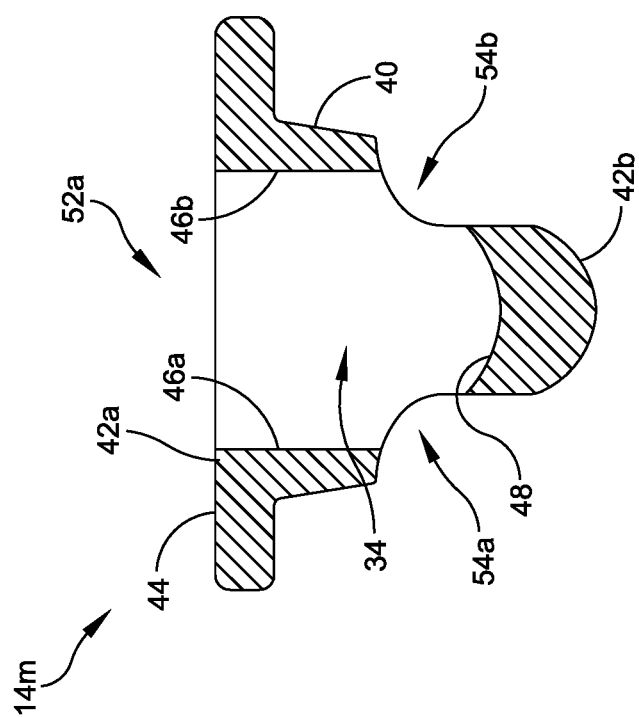

KNOTLESS SYNDESMOSIS SYSTEM

CROSS-REFERENCE TO RELATED APPLICATION

This application is continuation of U.S. patent application Ser. No. 16/333,634, filed Mar. 15, 2019, which is a U.S. national stage application under 35 U.S.C. § 371 of International Application No. PCT/US2016/066902, filed Dec. 15, 2016, the entireties of which are incorporated herein by reference.

BACKGROUND

Various injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, a first bone and a second bone must be maintained in a fixed position to allow the connective tissue to refuse.

Current suture systems include a suture anchor and one or more knots for maintaining sutures in a fixed position. Knots formed in the sutures can cause irritation during healing and may be subject to tearing due to friction or other forces applied to the knot. Current systems further require surgeons to form knots during surgery. Such systems are prone to failure and increase time of surgery.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 7 illustrates a knot capsule having a plurality of side loop openings, in accordance with some embodiments.

FIG. 8 illustrates a knot capsule having at least one angled surface defined within a knot cavity, in accordance with some embodiments.

FIG. 9 illustrates a knot capsule including a knot opening defined in a proximal cap having a diameter equal to the diameter of the knot cavity, in accordance with some embodiments.

FIG. 10 illustrates a knot capsule including a knot opening defined a proximal cap and at least one additional loop opening, in accordance with some embodiments.

FIG. 11 illustrates a knot capsule including a knot cavity defining at least one angled push ledge, in accordance with some embodiments.

FIG. 12 illustrates a knot capsule including a plurality of angle openings, in accordance with some embodiments.

FIGS. 13A and 13B illustrate a knot capsule including a generally circular loop opening and a channel formed in a sidewall of a body, in accordance with some embodiments.

FIGS. 14A and 14B illustrate knot capsule including a generally circular loop opening formed in a sidewall of a body, in accordance with some embodiments.

FIG. 15 illustrates a knot capsule having a generally pyramid-shaped body, in accordance with some embodiments.

DETAILED DESCRIPTION

Figure 1:
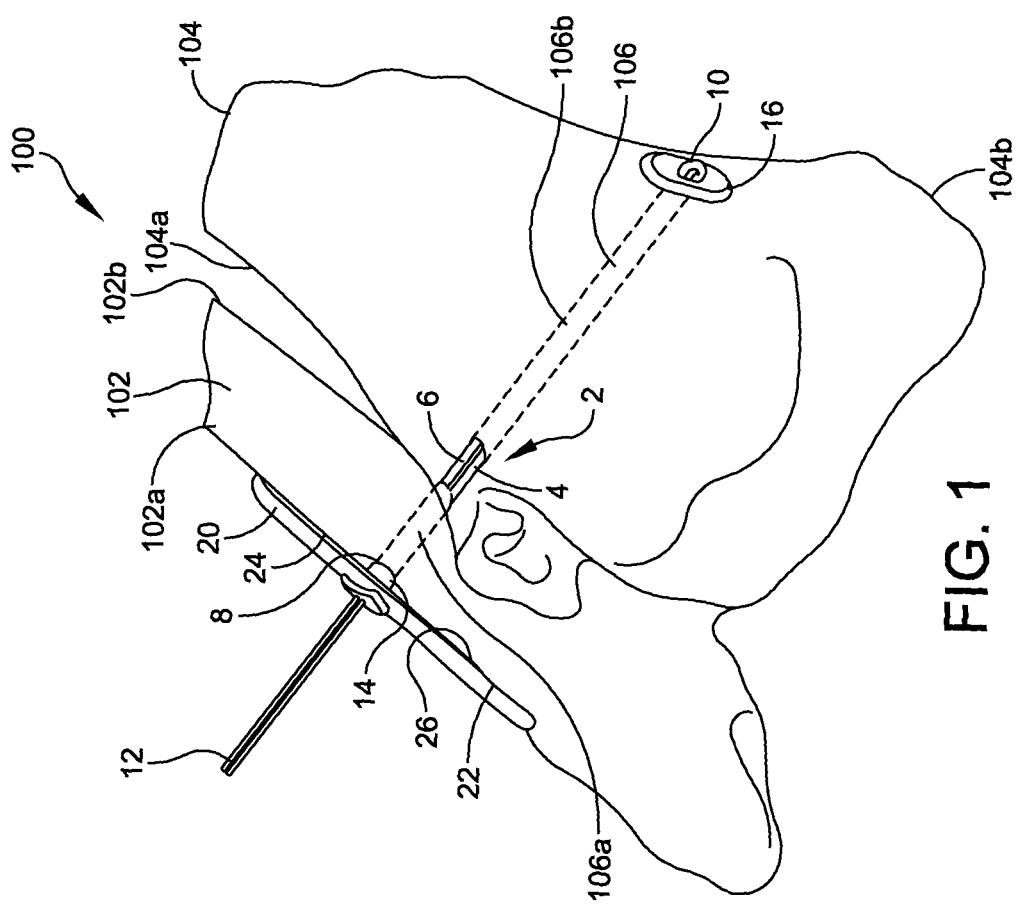
FIG. 1 illustrates a surgical site including first bone and a second bone coupled by an anchoring construct, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

In various embodiments, an anchoring construct including a flexible strand defining at least one adjustable loop is disclosed. The adjustable loop extends from a proximal end to a distal end. A knot capsule is coupled to the proximal end of the adjustable loop. The knot capsule includes an internal cavity sized and configured to receive a friction knot therein. The friction knot is coupled to the adjustable loop and is configured to transition from a first configuration to a second configuration. The adjustable loop 6 is adjustable when the friction knot is in the first configuration and is locked (or non-adjustable) when the friction knot is in the second configuration. The internal cavity defines one or more surfaces for adjusting the position of the friction knot on the adjustable loop and/or maintaining the friction knot in a fixed position when the friction knot is transitioned to the second configuration. In some embodiments, a flat button anchor is coupled to a distal end of the adjustable loop.

FIG. 1 illustrates a surgical site 100 including a first bone 102 and a second bone 104 coupled by an anchoring construct 2, in accordance with some embodiments. The anchoring construct 2 is configured to maintain the first bone 102 and a second bone 104 in a fixed position. The anchoring construct 2 includes a flexible strand 4, defining at least one loop 6 (see FIG. 2) extending from a proximal end 8 to a distal end 10. The flexible strand 4 can include any suitable material, such as, for example, one or more sutures, ribbons, ropes, etc. In some embodiments, an adjustment portion 12 extends proximally from the at least one loop 6. The adjustment portion 12 is configured to provide shortening (e.g., tightening) and/or lengthening (e.g., loosening) of the adjustable loop 6. Although embodiments are discussed herein having an anchoring construct 2 extending from a first bone 102 to a second bone 104, it will be appreciated that the anchoring constructs substantially disclosed and described herein can be used with any number of bones, include one bone, two bones, three bones, etc., and is within the scope of this disclosure and the appended claims.

In some embodiments, a proximal end 8 of the adjustable loop 6 is coupled to a knot capsule 14. The knot capsule 14 includes one or more openings for receiving the adjustable loop 6, as discussed in more detail below. For example, as discussed in more detail with respect to FIGS. 4A-4C, in some embodiments the knot capsule 14 includes a first loop opening and a second loop opening configured to receive the adjustable loop 6 therethrough. The knot capsule 14 anchors a proximal end 8 of the adjustable loop 6 to a first side 102a of the first bone 102 (such as, for example, a lateral side, a medial side, etc.)

In some embodiments, a distal end 10 of the adjustable loop 6 is coupled to a flat button anchor 16. The flat button anchor 16 can include one or more openings configured to receive a portion of a flexible loop 6 therethrough. The adjustable loop 6 is looped around and/or through a portion of the flat button anchor 16. The flat button anchor 16 anchors a distal end 10 of the adjustable loop 6 to a second side 104b of the second bone 104 (such as, for example, a medial side, a lateral side, etc.)

Figure 18:
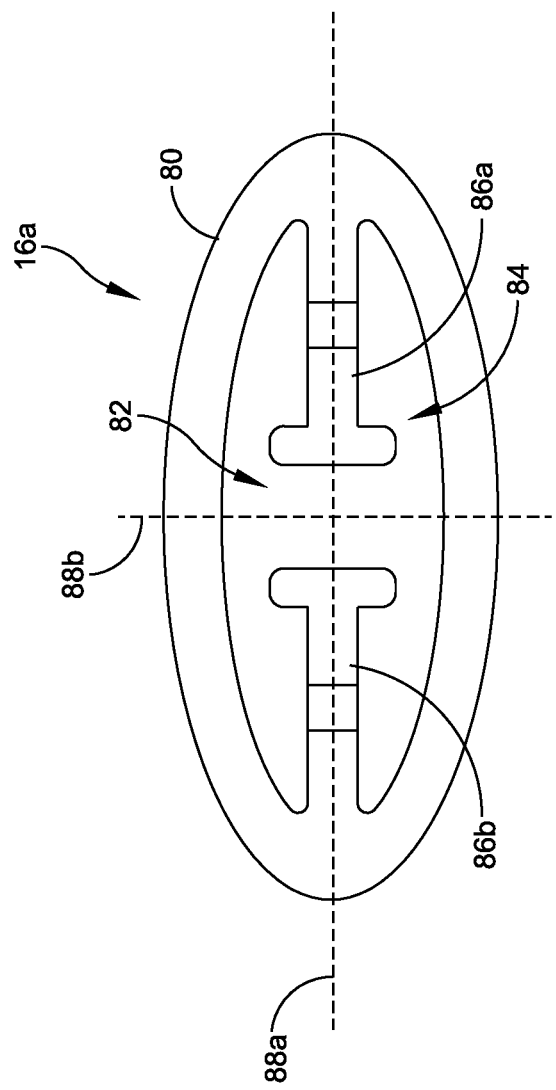
FIG. 18 illustrates a flat button implant, in accordance with some embodiments.

FIG. 18 illustrates a flat button anchor 16a, in accordance with some embodiments. The flat button anchor 16a includes a body 80 having a generally circular and/or oblong (e.g., oval) shape. The body 80 defines one or more cutouts 82. In the illustrated embodiment, the cutout 82 is a center cut-out defining an inner cavity 84. In other embodiments, the cutouts 82 extend from an outer surface of the body 80 towards a center point of the body 80. The cutout 82 defines one or more suture receiving posts 86a, 86b. In some embodiments, the flat button anchor 16a includes a first longitudinal axis 88a and a second longitudinal axis 88b. The length of the first longitudinal axis 88a can be greater and/or less than the length of the second longitudinal axis 88b. In some embodiments, the lengths of the longitudinal axes 88a, 88b can be selected such that the flat button anchor 16a can be passed through a bone tunnel 106 when the first longitudinal axis 88a is parallel to a longitudinal axis of the bone tunnel 106 but cannot pass through the bone tunnel 106 when the first longitudinal axis 88b is non-parallel and/or substantially perpendicular to the longitudinal axis of the bone tunnel 106.

Figure 19:
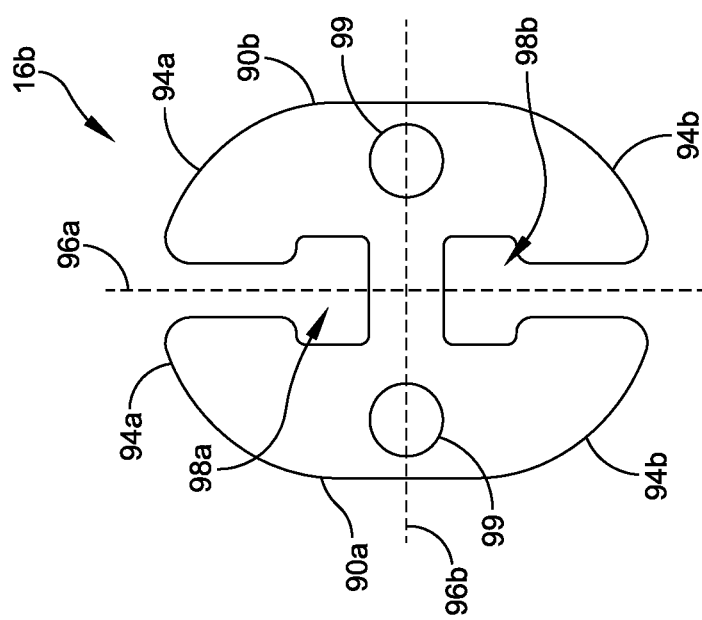
FIG. 19 illustrates a second flat button anchor, in accordance with some embodiments.

FIG. 19 illustrates flat button anchor 16b, in accordance with some embodiments. The flat button 16a includes a body 90 having a first side 90a and a second side 90b coupled by a center post 92. Each of the first side 90a and the second side 90b include a first arm 94a and a second arm 94b extending at a predetermined arc from the center post 92. Each of the arms 94a, 94b are sized and configured to receive a portion of an adjustable loop 6 thereabout. The flat button 16b is configured to couple a distal end of an adjustable loop 6 to a second bone 104. In some embodiments, the flat button anchor 16b defines one or more suture openings 98 sized and configured to receive an adjustment portion 12 of a suture therethrough. In some embodiments, the flat button anchor 16b includes a first longitudinal axis 96a and a second longitudinal axis 96b. The length of the first longitudinal axis 96a can be greater and/or less than the length of the second longitudinal axis 96b. In some embodiments, the lengths of the longitudinal axes 96a, 96b can be selected such that the flat button anchor 16a can be passed through a bone tunnel 106 when the first longitudinal axis 86a is parallel to a longitudinal axis of the bone tunnel 106 but cannot pass through the bone tunnel 106 when the first longitudinal axis 96a is non-parallel and/or substantially perpendicular to the longitudinal axis of the bone tunnel 106. In some embodiments, the flat button 16a includes one or more tool holes 99 sized and configured to interface with a tool for holding the flat button 16a prior to and/or during insertion or connection of the flat button 16a.

In some embodiments, a bone plate 20 is coupled to the first side 102a of the first bone 102. The bone plate 20 includes a body xtending between a first (or bone-contact) surface 24 and an opposing second (or outer) surface 26. The body 22 has a predetermined thickness. In some embodiments, the body 22 defines one or more knot capsule holes and/or one or more fastener holes, as discussed in more detail below with respect to FIG. 16. The bone plate 20 can be coupled to the first bone 102 prior to and/or simultaneously with the anchoring construct 2.

Figure 2:
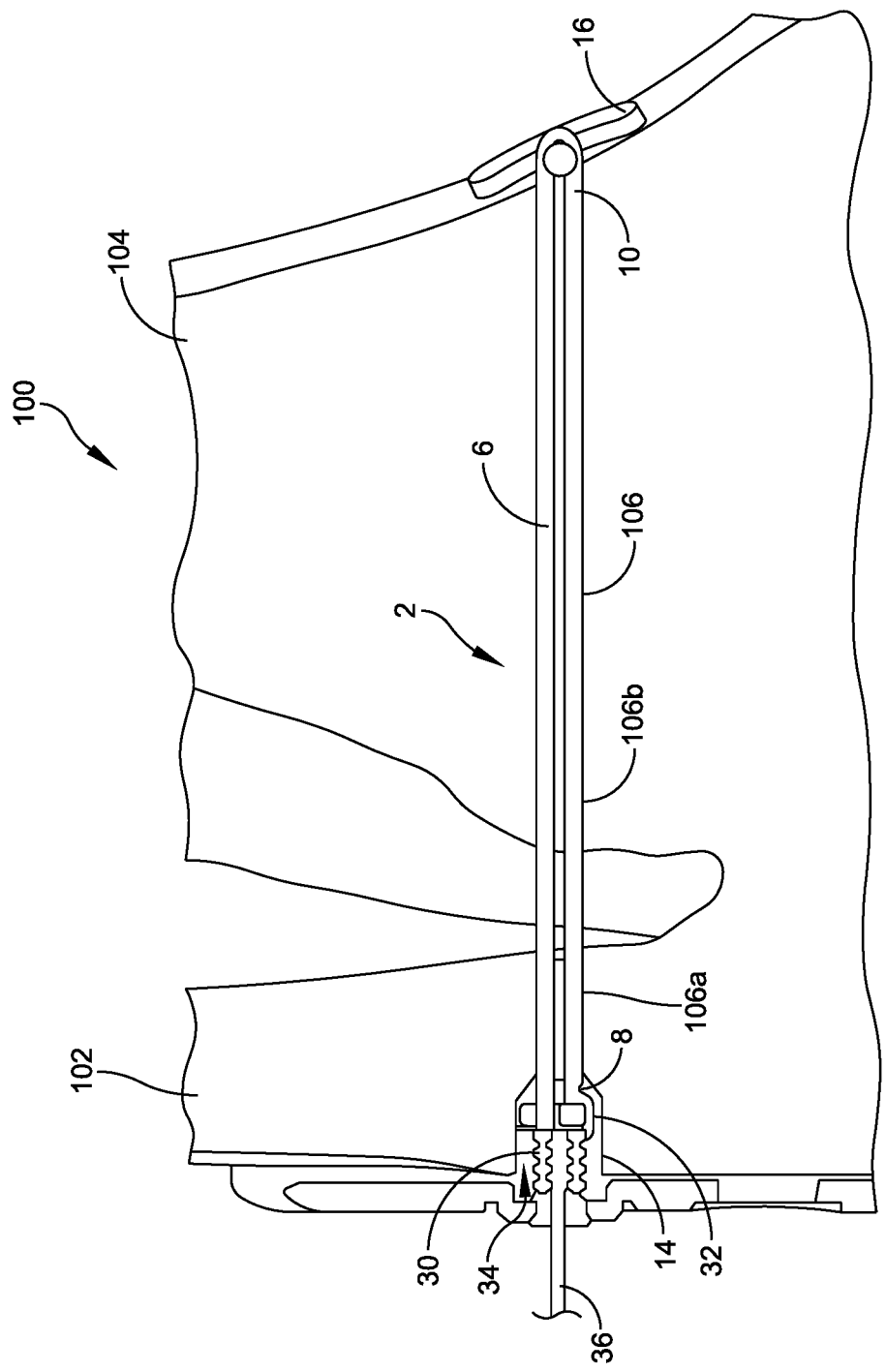
FIG. 2 is a cross-sectional view of the surgical site of FIG. 1, in accordance with some embodiments.

FIG. 2 shows a cross-sectional view of the surgical site 100 of FIG. 1, in accordance with some embodiments. The first adjustable loop 6 extends from the first side 102a of the first bone 102 to the second side 104b of the second bone 104 through a bone tunnel 106 defined in the first and second bones 102, 104, respectively. The bone tunnel 106 includes a first portion 106a extending from the first side 102a to a second side 102b of the first bone 102 and a second portion 106b extending from a first side 104a to the second side 104b of the second bone 104. The bone tunnel 106 can be formed using any suitable surgical device, such as, for example, a drill, a k-wire, an impactor, a needle, and/or any other suitable device.

In some embodiments, the bone tunnel 106 has a diameter sufficient to allow the flat button anchor 16 to pass through the bone tunnel 106 at a first orientation. For example, as discussed in more detail herein, in some embodiments the flat button anchor 16 includes an oblong (or elliptical) shape having a first diameter greater than a second diameter. When the oblong flat button anchor 16 is positioned at the first orientation (such as with the long axis of the elliptical parallel to an axis of the bone tunnel 106), the flat button anchor 16 is able to pass through the bone tunnel 106. When the flat button anchor 16 is positioned at a second orientation (e.g., with the long axis of the elliptical substantially perpendicular to the axis of the bone tunnel 106), the flat button anchor 16 is prevented from passing through the bone tunnel 106. In other embodiments, the bone tunnel 106 has a diameter sufficient to allow passage of an adjustable loop 6 and one or more passage elements, such as a needle. In other embodiments, the flat button anchor 16 can be coupled to one or more of the adjustable loops 6 after insertion of the adjustable loop 6 through the bone tunnel 106.

In some embodiments, the adjustable loop 6 is coupled to a friction knot 30 positioned within the knot capsule 14. The adjustable loop 6 passes through at least one loop opening 32 formed in the knot capsule 14. The at least one loop opening 32 extends from an outer surface of the knot capsule 14 to a knot cavity 34 defined by a body of the knot capsule 14. The friction knot 30 is positioned within the knot cavity 34 and is coupled to a portion of the adjustable loop 6. In some embodiments, the friction knot 30 is formed around the portion of the adjustable loop 6, prior to insertion of the friction knot 30 within the knot capsule 14.

The adjustable loop 6 is shortened and/or lengthened to position the first bone 102 and the second bone 104 in a predetermined spaced relationship. In some embodiments, an adjustment portion 12 of the flexible strand 4 extends through a cap opening 52 (see FIG. 4B) formed in a proximal cap of the knot capsule 14. The adjustment portion 12 can be manipulated (e.g., pulled) to shorten the diameter of the adjustable loop 6 to position the first bone 102 and the second bone 104. When the first bone 102 and the second bone 104 are positioned in the predetermined spaced arrangement, the friction knot 30 can be locked (i.e., tightened) to prevent movement of the adjustable loop 6. For example, in some embodiments, the friction knot 30 locks the adjustable loop 6 at the selected length to maintain the first and second bones 102, 104 in the predetermined spaced arrangement.

In some embodiments, a locking strand 36 extends from the friction knot 30 to allow locking and/or unlocking of the friction knot 30. The locking strand 36 can extend through an opening formed in the knot capsule 14, such as the cap opening 52. The locking strand 36 is configured to tighten the friction knot 30 to lock the adjustable loop 6 at the selected length. In other embodiments, the locking strand 36 is omitted and the friction knot 30 is self-locking, as discussed in more detail below.

Figure 3:
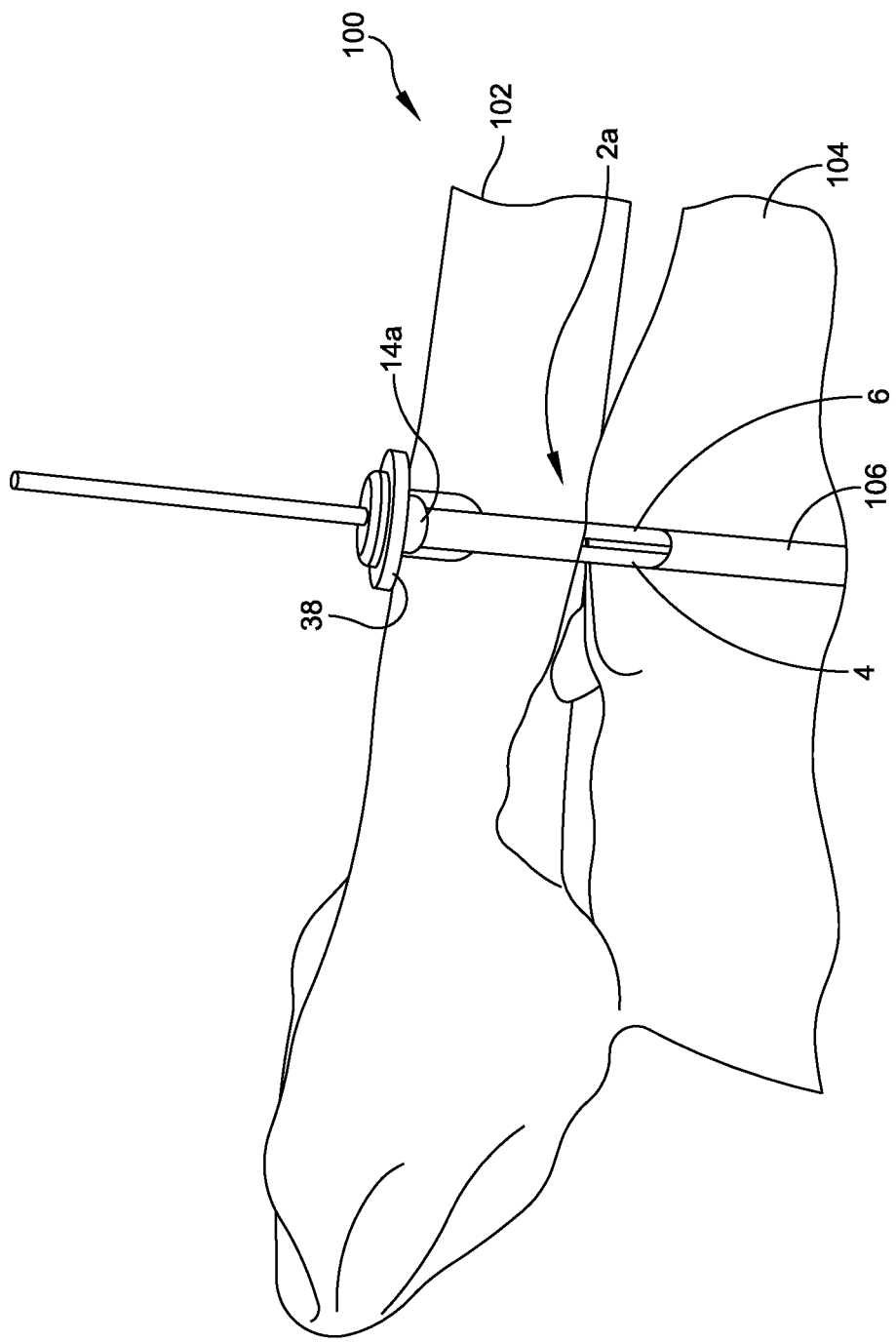
FIG. 3 illustrates a surgical site including an anchoring construct having a knot capsule coupled to a capsule washer, in accordance with some embodiments.

FIG. 3 illustrates the surgical site 100 including an anchoring construct 2*a* having a knot capsule 14*a* coupled to a capsule washer 38. The anchoring construct 2*a* is similar to the anchoring construct 2 discussed above, and similar description is not repeated herein. In some embodiments, the capsule washer 38 is used when a bone plate 20 is omitted. The capsule washer 38 is configured to maintain the knot capsule 14*a* at a proper depth/spacing with respect to the first bone 102 (e.g., to mimic the height/thickness of a bone plate 20) to prevent subsidence of the knot capsule 14*a*. In some embodiments, the capsule washer 38 has a diameter greater than the diameter of the bone tunnel 106. The capsule washer 38 can include any suitable material, such as, for example, a non-compressible material (e.g., metal, ceramic, etc.) and/or a compressible material (e.g., bio-compatible plastic, silicon, gel, etc.).

Figure 4A:
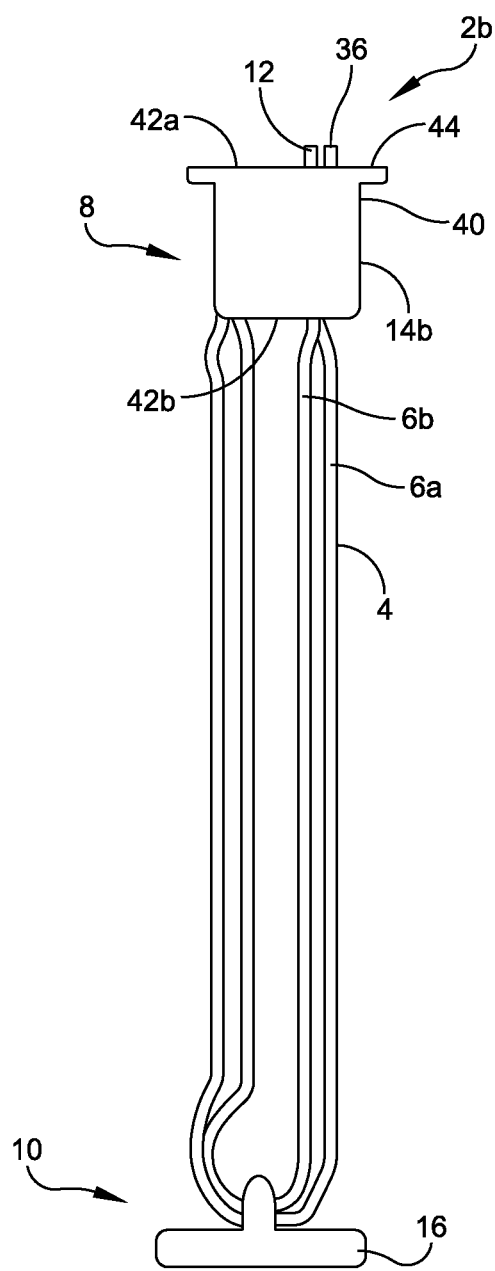
FIG. 4A illustrates an anchoring construct including a knot capsule configured to receive a friction knot therein, in accordance with some embodiments.
Figure 4C:
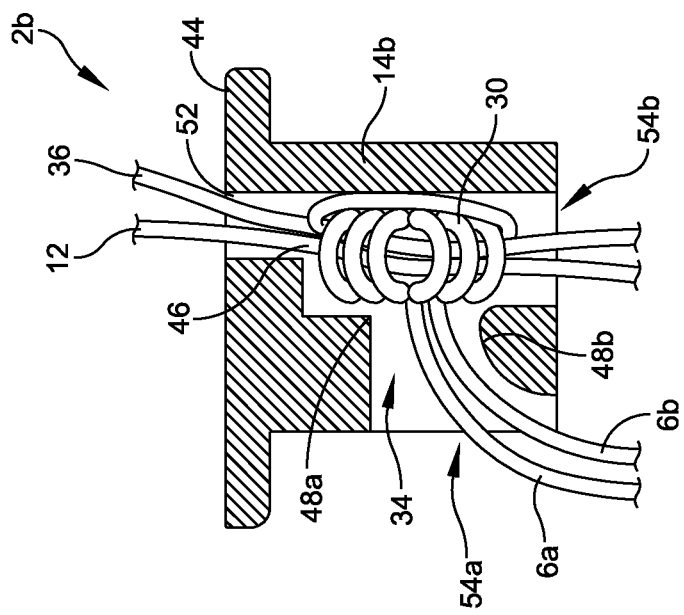
FIG. 4C illustrates a cross-sectional view of the knot capsule of the suture construct of FIG. 4A having a friction knot in a first configuration, in accordance with some embodiments.
Figure 4B:
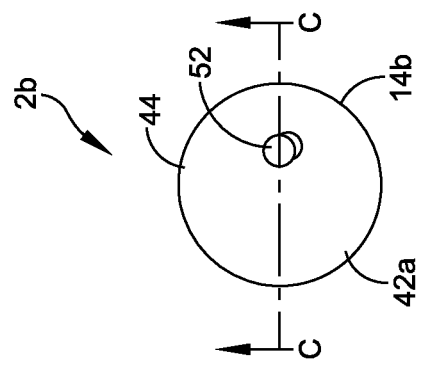
FIG. 4B illustrates a top view of the suture construct of FIG. 4A, in accordance with some embodiments.
Figure 5B:
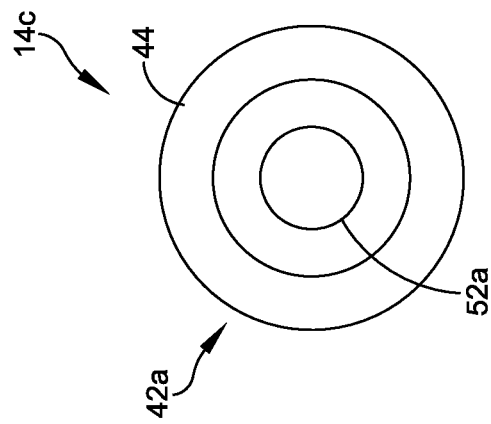
FIG. 5B is a bottom view of the knot capsule of FIG. 5A, in accordance with some embodiments.
Figure 5A:
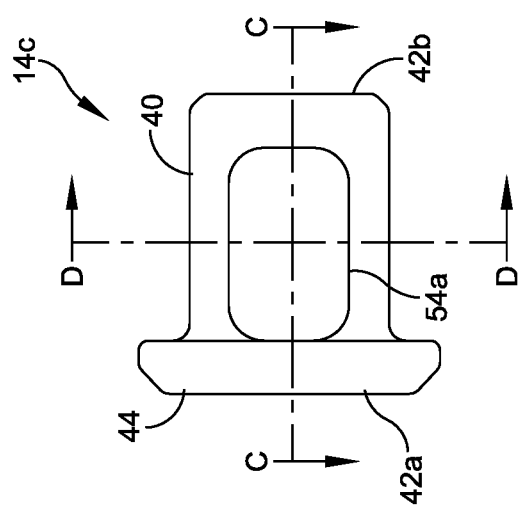
FIG. 5A illustrates one embodiment of a knot capsule having at least one side opening, in accordance with some embodiments.
Figure 5D:
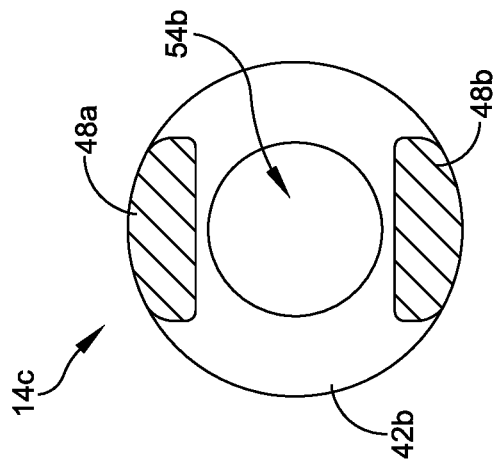
FIG. 5D is a cross-sectional view of the knot capsule of FIG. 5A, in accordance with some embodiments.
Figure 5C:
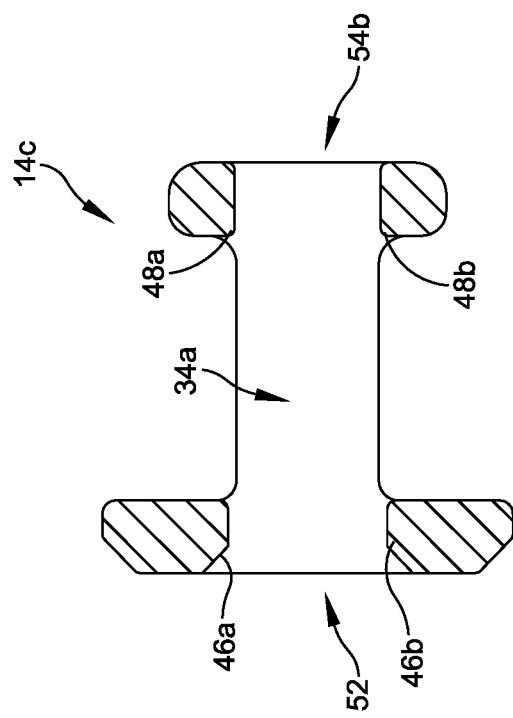
FIG. 5C is a cross-sectional view of the knot capsule of FIG. 5A, in accordance with some embodiments.
Figure 6B:
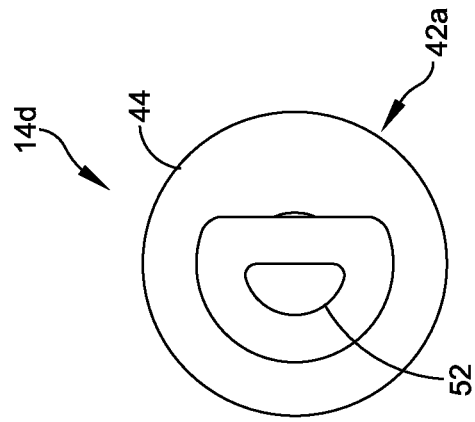
FIG. 6B is a bottom view of the knot capsule of FIG. 6A, in accordance with some embodiments.
Figure 6A:
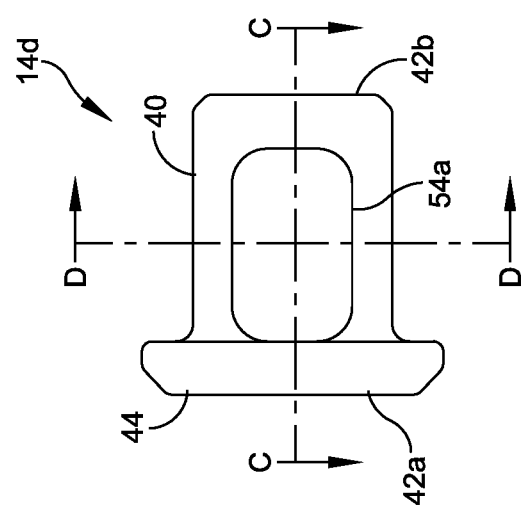
FIG. 6A illustrates one embodiment of a knot capsule having at least one side opening and a D-shaped top opening, in accordance with some embodiments.
Figure 6C:
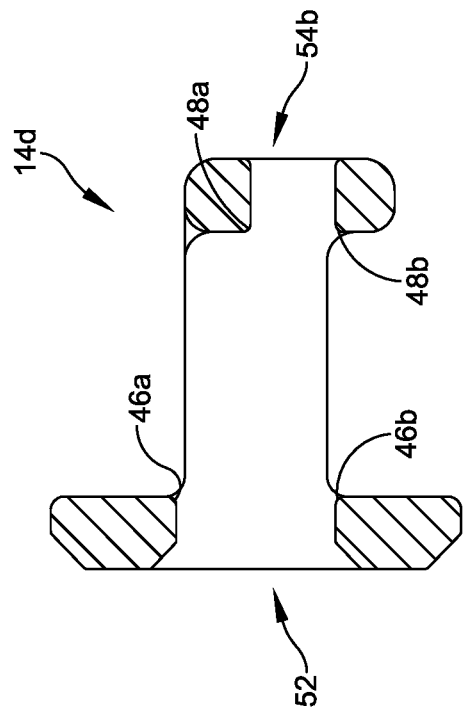
FIG. 6C is a cross-sectional view of the knot capsule of FIG. 6A, in accordance with some embodiments.
Figure 6D:
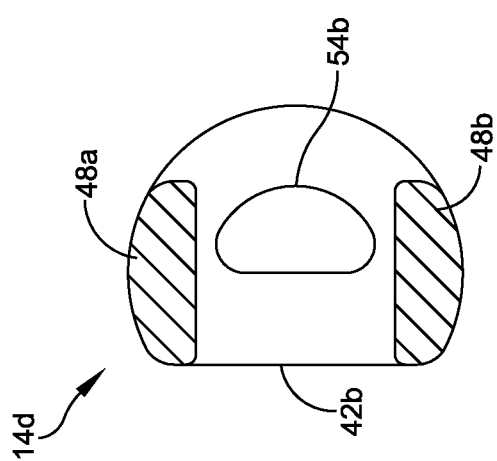
FIG. 6D is a cross-sectional view of the knot capsule of FIG. 6A, in accordance with some embodiments.

FIGS. 4A-4C illustrate an anchoring construct 2*b*, in accordance with some embodiments. The anchoring construct 2*b* includes a flexible strand 4 defining a first adjustable loop 6*a* and a second adjustable loop 6*b*. The first and second adjustable loops 6*a*, 6*b* extend from a proximal end 8 to a distal end 10 of the anchoring construct 2*b*. Further, the first and second adjustable loops 6*a*, 6*b* are coupled to a knot capsule 14*b* at the proximal end 8 and a flat button anchor 16 at the distal end 10 of the anchoring construct 2*b*. Although two adjustable loops 6*a*, 6*b* are illustrated, it will be appreciated that the flexible strand 4 can define any number of adjustable loops.

In some embodiments, the knot capsule 14*b* includes a body 40 having a proximal end 42*a* and a distal end 42*b*. The body 40 can have any suitable shape, such as, for example, a substantially cylindrical shape, rectangular shape, pyramidal shape, oblong shape, etc. The body 40 has a first diameter. A proximal cap 44 is coupled to a proximal end 42*a* of the body. The proximal cap has a second diameter, where the first diameter is less than the second diameter, such that movement through the bone tunnel is limited.

The body 40 defines a knot cavity 34 therein. The knot cavity 34 is sized and configured to receive a friction knot 30 and a portion of each of the adjustable loops 6*a*, 6*b* therein. The friction knot 30 is positioned within the knot cavity 34 and coupled to the adjustable loops 6*a*, 6*b* in a functional arrangement. The friction knot 30 is configured to transition from a first (or loose) configuration to a second (or tight) configuration. In the first configuration (as shown in FIG. 4C), the friction knot 30 is loosely coupled to the adjustable loops 6*a*, 6*b* such that the adjustable loops 6*a*, 6*b* can be shortened and/or lengthened, for example, by adjustment portions 12 of the flexible strand 4.

As discussed above, when the adjustable loops 6*a*, 6*b* are adjusted to a predetermined length to maintain a first bone 102 and a second bone 104 in a predetermined spacing, the friction knot 30 is transitioned to the second configuration. In the second configuration (not shown), the friction knot 30 is tightly coupled to the adjustable loops 6*a*, 6*b* such that the adjustable loops 6*a*, 6*b* cannot be shortened and/or lengthened. The friction knot 30 maintains the adjustable loops 6*a*, 6*b* at the predetermined length. The friction knot 30 can be permanently locked (e.g., requires cutting the flexible strand 4 to remove) and/or can be releasably locked to the adjustable loops 6*a*, 6*b*. Releasable locking systems include a release strand as described in more detail herein.

The friction knot 30 can be any suitable friction knot. For example, in some embodiments, the friction knot 30 can include a Prusik knot, a Klemheist knot, a Distel hitch, a Blake's hitch knot, a clove hitch knot, a Tennessee slider knot, a Nice knot, and/or any other suitable friction knot. The friction knot 30 is formed by a second flexible strand tied around the first flexible strand 4 to define the friction knot 30. In some embodiments, the friction knot 30 is a self-tightening friction knot.

In some embodiments, the knot cavity 34 can include one or more surfaces configured to assist in tightening and/or positioning of the friction knot 30. For example, in the illustrated embodiment, the knot cavity 34 defines one or more push ledges 46 and one or more impingement surfaces 48*a*, 48*b*. Although embodiments are discussed herein differentiating the push ledges 46 and the impingement surfaces 48*a*, 48*b*, it will be appreciated that designation of a surface as a push ledge 46 does not prevent that surface from alternatively and/or additionally serving as an impingement surface 48*a*, 48*b* and designation of a surface as an impingement surface 48*a*, 48*b* does not prevent that surface from alternatively and/or additionally serving as a push ledge 46.

As shown in FIG. 4C, the illustrated embodiment includes a push ledge 46 positioned in a proximal portion of the knot cavity 34. The push ledge 46 is configured to apply a moving force to the friction knot 30 that causes the friction knot 30 to transit (or move) along the adjustable loops 6a, 6b when the adjustable loops 6a, 6b are adjusted. For example, in some embodiments, an adjustment portion 12 of a flexible strand 4 extends through a cap opening 52 defined in a cap 44 coupled to the proximal portion of the body 40. When a force is applied to the adjustment portion 12 to shorten the adjustable loops 6a, 6b, the push ledge 46 applies a force to the friction knot 30 to cause the friction knot 30 to transit along at least one of the adjustable loops 6a, 6b and maintain a fixed position within the knot capsule 14b with respect to the adjustable loops 6a, 6b. For example, in some embodiments, the friction knot 30 is maintained at a proximal-most portion 8 of the adjustable loop 6.

In some embodiments, the knot cavity 34 includes at least one impingement surface 48. The impingement surfaces 48a, 48b are configured to assist in tightening/locking of the friction knot 30 when a force is applied to a trailing end of the friction knot 30, such as a locking strand 36. For example, in some embodiments, the friction knot 30 includes the locking strand 36 configured to apply a locking force to the friction knot 30. When the friction knot 30 is transitioned to the second configuration (e.g., tightened), the friction knot 30 is positioned between the impingement surfaces 48a, 48b. For example, in some embodiments, the tightening of the friction knot 30 and the adjustable loops 6a, 6b causes the friction knot 30 to be positioned between the impingement surfaces 48a, 48b. The impingement surfaces 48a, 48b apply a force to the friction knot 30 and maintain the friction knot 30 in a fixed position between the impingement surfaces 48a, 48b.

In some embodiments, the push ledge 46 and the impingement surfaces are configured to assist in positioning and locking of the friction knot 30 For example, FIG. 4C illustrates the friction knot 30 in a first, loose configuration. As the adjustable loops 6a, 6b are shortened (e.g., tightened), the friction knot 30 is pulled into contact with the push ledge 46. The push ledge 46 causes the friction knot 30 to slide or transit on the adjustable loops 6a, 6b during adjustment. When the adjustable loops 6a, 6b are shortened to a predetermined length, a locking force is applied to lock the friction knot 30 onto the adjustable loops 6a, 6b. Locking of the friction knot 30 (i.e., transition to the second configuration) causes the friction knot 30 to compress such that a portion of the friction knot 30 fits between the first and second impingement surfaces 48a, 48b. The friction knot 30 is pulled into contact with the impingement surfaces by a force applied by the adjustable loops 6a, 6b. The impingement surfaces 48a, 48b further lock the friction knot 30 and maintain the knot in a fixed position within the knot cavity 34. In other embodiments, the push ledge 46 and/or the impingement surfaces 48a, 48b can be configured to automatically tighten the friction knot 30 when the adjustable loops 6a, 6b apply a predetermined force to the friction knot 30.

In some embodiments, the proximal cap 44 defines a cap opening 52. The cap opening 52 is sized and configured to receive one or more flexible strands therethrough, such as an adjustment portion 12 coupled to the adjustable loops 6a, 6b, a locking strand 36, and/or any other suitable flexible strand. In the illustrated embodiment, the cap opening 52 is a circular opening, although it will be appreciated that the cap opening 52 can have any suitable shape, such as a circular, square, oblong, triangular, etc. The cap opening 52 has a diameter sufficient to allow the flexible strands, such as adjustment portion 12 and locking strand 36 therethrough, but not large enough for friction knot 30 to pass through.

In some embodiments, the one or more flexible strands 12, 36 extending through the cap opening 52 can be cut after the friction knot 30 is tightened (e.g., transitioned to the second configuration) to maintain the adjustable loops 6a, 6b at a fixed length. In some embodiments, one or more additional knots can be formed by a surgeon using the one or more flexible strands 12, 36 extending through the cap opening 52. The one or more additional knots provide additional locking of the friction knot 30 to prevent loosening and/or releasing of the friction knot 30.

In some embodiments, the body 40 defines one or more loop openings 54a, 54b sized and configured to allow the flexible strand 4 of the adjustable loops 6a, 6b to pass from an outer surface of the knot capsule 14b to the knot cavity 34. For example, in the embodiment illustrated in FIGS. 4A-4C, the body 40 defines a first loop opening 54a on a first side of the body 40 and a second opening 54b in a center of the distal end 42b of the body 40. The adjustable loops 6a, 6b pass through the first opening 54a, are coupled to the friction knot 30 (for example, by passing through a channel defined by the friction knot 30, and exit the knot cavity 34 through the second opening 54b. In some embodiments, the body 40 can define additional openings for receiving one or more additional adjustable loops 6a, 6b. Additional embodiments of knot capsules 14c-14m are discussed with respect to FIGS. 5A-15 below.

In some embodiments, an locking knot 56 can be formed above the cap opening 52 to further lock the adjustable loop 6 at the selected length. For example, in some embodiments, a locking knot 56 can be formed form excess adjustment strand 12 extending through the cap opening 52. The locking knot 56 can include any suitable knot, such as, for example, a square knot, a sheet bend knot, a fisherman's knot (single or double), and/or any other suitable knot. In some embodiments, excess adjustment strand 12 extending from the cap opening 52 and/or the locking knot 56 can be cut or otherwise removed after locking the adjustable loop 6 at the predetermined length.

FIGS. 5A-5D illustrates a knot capsule 14c including a side loop opening 54a and a bottom loop opening 54b. The knot capsule 14c is similar to the knot capsules 14-14b discussed above, and similar description is not repeated herein. The knot capsule 14c includes a cylindrical knot cavity 34a. First and second push ledges 46a, 46b are positioned at a proximal end of the knot cavity 34a and first and second impingement surfaces 48a, 48b are positioned at a distal end of the knot cavity 34a. The distal end 42b of the body 40 defines the second loop opening 54b. In some embodiments, a proximal cap 44 defines a knot opening 52a sized and configured to receive the friction knot 30 therein. A trailing end, such as an locking strand 36, extends from the friction knot 30 through the knot opening 52a. In some embodiments, an adjustment portion 12 of a flexible strand 4 further extends through the knot opening 52a.

FIGS. 6A-6D illustrate a knot capsule 14d including a D-shaped side loop opening 54b. The knot capsule 14d is similar to the knot capsule 14c discussed above, and similar description is not repeated herein. The distal end 42b of the body 40 defines the D-shaped loop opening 54b. The D-shaped loop opening 54b is sized and configured to allow a flexible strand 4 (not shown) defining one or more adjustable loops 6a, 6b to pass therethrough. In some embodiments, the edges of the D-shaped loop opening 54b are smooth to allow for sliding of the flexible strand 4 during tightening and/or loosening of the adjustable loops 6a, 6b. A first impingement surface 48a is positioned on a first side of the D-shaped loop opening 54b and the second side of the D-shaped loop opening 54b defines a second impingement surface 48b. The impingement surfaces 48a, 48b are configured to apply an impingement force to a friction knot 30, as discussed above.

In some embodiments, a proximal cap 44 of the body 40 defines a D-shaped opening 52 sized and configured to receive an adjustment portion 12 of the flexible strand 4 and/or a locking strand 36 extending from a friction knot 30 therethrough. A first push ledge 46a and a second push ledge 46b are positioned on either side of the D-shaped opening 52 and are configured to apply a push force to cause the friction knot 30 to slide along the adjustable loops 6a, 6b, as discussed above.

FIG. 7-15 illustrate various knot capsules 14e-14m, in accordance with various embodiments. The knot capsules 14e-14m are similar to the knot capsules 14-14d discussed above, and similar description is not repeated herein. The knot capsule 14e illustrated in FIG. 7 includes a first side loop opening 54a and a second side loop opening 54b. The loop openings 54a, 54b are sized and configured to allow a portion of each of the adjustable loops 6a, 6b to extend therethrough. An impingement surface 48 is defined between the first loop opening 54a and the second loop opening 54b. The knot capsule 14e further includes a first push ledge 46a (similar to the push ledge 46 of knot capsule 14b) and a second push ledge 46b. The first and second push ledges 46a, 46b apply a pushing force to a friction knot 30, as discussed above. In some embodiments, a third push ledge 46c is configured to apply a pushing force to the friction knot 30 and is further configured to apply an impingement force to the friction knot 30, e.g., the push ledge 46c is a dual-purpose surface acting as both a push ledge and an impingement surface. In some embodiments, each of the push ledges 46a-46c and/or impingement surfaces 48 are parallel with the proximal and distal ends 42a, 42b of the body 40.

FIG. 8 illustrates a knot capsule 14f including an angled surface 46b. The angled surface 46b is angled with respect to the proximal and distal ends 42a, 42b of the body 40. In some embodiments, the angled surface 46b is further angled with respect to one or more push ledges 46a. The angled surface 46b is configured to act as a push ledge during adjustment of the adjustable loops 6a, 6b and act as an impingement surface when the friction knot 30 is tightened.

FIG. 9 illustrates a knot capsule 14g including a knot opening 52a in the proximal cap 44 having a diameter equal to the maximum diameter of the knot cavity 36. The knot opening 52a is sized and configured to allow a friction knot 30 to be accessed, for example, to allow the friction knot 30 to be loosened after tightening to allow readjustment of the adjustable loops 6a, 6b. The knot cavity 34 defines first and second push ledges 46a, 46 and first and second angled impingement surfaces 48a, 48b.

FIG. 10 illustrates a knot capsule 14h similar to the knot capsule 14g discussed in conjunction with FIG. 9, and similar description is not repeated herein. The knot capsule 14h includes an additional loop opening 54c. The additional loop opening 54c is configured to receive at least a portion of one or more of the flexible loops 6a, 6b defined by a flexible strand 4. For example, in some embodiments, a first adjustable loop 6a includes a flexible strand 4 extending through the first loop opening 54a and the second loop opening 54b and a second adjustable loop 6b includes a flexible strand 4 looped through the second loop opening 54b and the third loop opening 54c, although it will be appreciated that additional configurations are within the scope of this disclosure.

FIG. 11 illustrates knot capsule 14i including angled push ledges 46a, 46b. The angled push ledges 46a, 46b are configured to translate the friction knot 30 along the adjustable loops 6a, 6b during adjustment (e.g., tightening/loosening) of the adjustable loops 6a, 6b. A first impingement surface 48a and a second impingement surface 48b are configured to lock the friction knot 30 when the friction knot 30 is transitioned to the second, tightened configuration.

FIG. 12 illustrates a knot capsule 14j including a plurality of angled openings 52a, 52b, 54a, 54b. A cap opening 52a extends form the knot cavity 34 through the proximal cap 44 of the body 40 at a first angle. The cap opening 52a is sized and configured to receive one or more portions of a flexible strand, such as an adjustment portion 12, a locking strand 36, and/or any other suitable flexible strand portion. A knot opening 52b extends from the knot cavity 34 through the proximate cap 44 and a portion of the sidewall of the body 40 at a second angle. The knot opening 52b is sized and configured to allow a friction knot 30 to pass therethrough. For example, in some embodiments, the knot opening 52b is sized and configured to allow a user to remove the friction knot 30 from the knot cavity 34 to release the friction knot 30 from a locked position for readjustment of the adjustable loops 6a, 6b.

In some embodiments, a first loop opening 54a extends from the knot cavity 34 through a distal end 42b of the body 40 at a third angle and a second loop opening 54b extends from the knot cavity 34 through the distal end 42b of the body 40 at a fourth angle. The first and second loop openings 54a, 54b are each configured to receive a portion of one or more adjustable loops 6a, 6b therethrough. The knot cavity 34 further defines a plurality of push ledges 46a-46d and a plurality of impingement surfaces 48a, 48b.

FIGS. 13A-13B illustrate a knot capsule 14k including a circular loop opening 54a formed in a sidewall of the body 40. The circular loop opening 54a is sized and configured to allow passage of a friction knot 30. In some embodiments, the friction knot 30 can be removed from the knot cavity 34 to release (e.g., loosen) the friction knot 30 after tightening and/or to tighten the friction knot 30. The outer surface of the body 40 defines a channel 58 configured to receive a portion of an adjustable loop 6a, 6b therein. FIGS. 14A-14B illustrate a knot capsule 14l similar to the knot capsule 14k of FIGS. 13A-13B but without the channel 58.

FIG. 15 illustrates a pyramidal knot capsule 14m, in accordance with some embodiments. The pyramidal knot capsule 14m is similar to the knot capsule 14b discussed above with respect to FIGS. 4A-4C, and similar description is not repeated herein. The pyramidal knot capsule 14m includes a body 40a defining a pyramidal shape between a proximal end 42a and a distal end 42b. A first loop opening 54a is defined on a first side of the body 40a and a second loop opening 54b is defined on a second side of the body 40b. In some embodiments, the proximal end 42a of the body 40a defines a knot opening 52a. The knot opening 52a is sized and configured to receive a friction knot therethrough, as discussed above.

Figure 16:
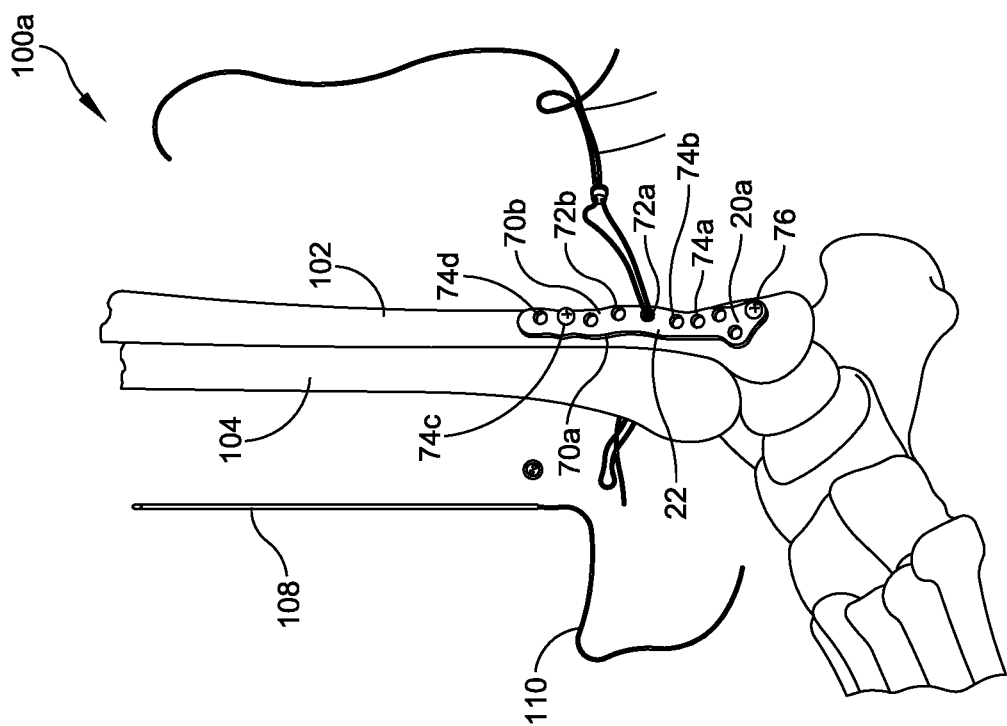
FIG. 16 illustrates a bone plate coupled to a first side of a first bone by an anchoring construct, in accordance with some embodiments.

FIG. 16 illustrates an anatomical structure 100a having a first bone 102 positioned with respect to a second bone 104 by a bone plate 20a and an anchor construct 2a. The bone plate 20a includes a body 22 extending between a bone facing surface 70a and an outer surface 70b. A plurality of capsule openings 72a, 72b sized and configured to receive a portion of a knot capsule 14-14m therethrough, as discussed above in conjunction with FIGS. 1-2. In some embodiments, an anchor construct 2a is inserted through a selected one 72a of the plurality of capsule openings 72a, 72b. The anchoring construct 2a maintains the position of the bone plate 20a with respect to the first bone 102 and further positions the first bone 102 and the second bone 104 in a predetermined spaced arrangement.

In some embodiments, the bone plate 20a includes one or more fastener holes 74a-74d extending from the outer surface 70b to the bone facing surface 70a. The fastener holes 74a-74d are sized and configured to receive one or more fasteners 76 therethrough. The fasteners 76 are configured to extend into the first bone 102 and further anchor the bone plate 20a to the first bone 102. In some embodiments, the fasteners 76 are configured to anchor the bone plat 20a to the first bone 102 prior to insertion of the anchoring construct 2a through a capsule opening 72a, 72b.

In some embodiments, the flexible strand 4 of the anchor construct 2a is inserted through the capsule opening 72a in the bone plate 20a and the first and second bones 102, 104 using a needle 108 coupled to the flexible strand 4 by a flexible pull strand 110. In some embodiments, the needle 108 is inserted through a bone tunnel 106 preformed in the first and second bones 102, 104. In other embodiments, the needle 108 is configured to form a bone tunnel 106 simultaneously with the insertion of the needle 108 through the first and second bones 102, 104.

Figure 17:
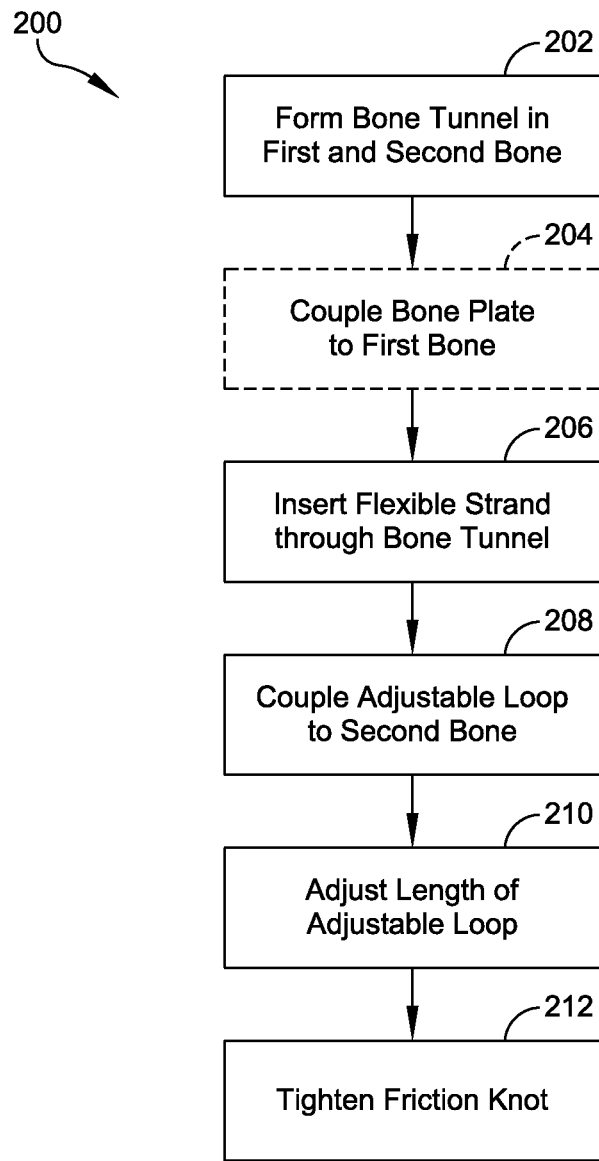
FIG. 17 illustrates a method of positioning a first bone and a second bone using an anchoring construct, in accordance with some embodiments.

FIG. 17 illustrates a method 200 of positioning a first bone 102 and a second bone 104 using an anchor construct 2, in accordance with some embodiments. The method 200 is discussed with reference to FIGS. 1-4C and 16-17. At step 202, a bone tunnel 106 is formed through a first bone 102 and a second bone 104. The bone tunnel 106 can be formed using any suitable device, such as, for example, a drill, a k-wire, a needle, etc. In some embodiments, step 202 is performed simultaneously with one more later steps, such as step 206 discussed below.

At optional step 204, a bone plate 20 is coupled to the first bone 102. The bone plate 20 includes one or more knot capsule openings 72a, 72b and one or more fastener holes 74a-74d. The bone plate 20 can be coupled to the first bone 102 using one or more fasteners 76 inserted through one or more of the fastener holes 74a-74d. In other embodiments, the bone plate 20 can be temporarily coupled to the first bone 102 by, for example, a k-wire or other temporary fixation device.

At step 206, an anchor construct 2 is coupled to the first bone 102 and the second bone 104. The anchor construct 2 is coupled to the first and second bones 102, 104 by inserting a flexible strand 4 defining at least one adjustable loop 6 through the bone tunnel 106. In some embodiments, a distal end 10 of the adjustable loop 6 is coupled to a flat button anchor 16. The flat button anchor 16 can be coupled to the distal end 10 of the adjustable loop 6 prior to insertion of the adjustable loop 6 through the bone tunnel 106. In such embodiments, the flat button anchor 16 is sized and configured for insertion through the bone tunnel 106 in at least a first configuration and is sized and configured to prevent movement through the bone tunnel 106 in a second configuration. In some embodiments, the flat button anchor 16 is coupled to the distal end 10 of the adjustable loop 6 after insertion of the adjustable loop 6 through the bone tunnel 106.

At step 208, the distal end 10 of the adjustable loop 6 is coupled to the second bone. For example, in some embodiments, the flat button anchor 16 is coupled to the adjustable loop 6 and positioned against an outer edge of the second bone 104.

At step 210, the adjustable loop 6 is shortened to reduce the distance between the first bone 102 and the second bone 104 to a predetermined spacing. The adjustable loop 6 can be shortened by, for example, an adjustment portion 12 extending through a cap opening 52 formed in proximal cap 44 of the knot capsule 14-14m. Applying a proximal force to the adjustment portion 12 shortens the adjustable loop 6. It will be appreciated that additional methods can be used to shorten the adjustable loop 6, such as, for example, pushing the proximal end 8 of the adjustable loop 6 through one or more openings of the knot capsule 14-14m and manually adjusting the length of the adjustable loop 6.

At step 212, the friction knot 30 is tightened to maintain the adjustable loop 6 at the selected length such that the first bone 102 and the second bone 104 are maintained at the predetermined spacing. In some embodiments, the friction knot 30 is tightened by applying a force to a locking strand 36 extending from the friction knot 30. In some embodiments, the friction knot 30 further interacts with one or more impingement surfaces 54a, 54b defined within the knot cavity 34 to maintain the friction knot 30 in a locked position within the knot cavity 34. In some embodiments, tension applied to the adjustable loop 6 by pulling on an adjustment portion 12 can automatically lock the friction knot 30.

In various embodiments, an anchor is disclosed. The anchor includes a flexible strand defining a first loop. A friction knot is coupled to a proximal end of the first loop. The friction knot is configured to allow adjustment of the first loop in a first configuration and is configured to prevent adjustment of the first loop in a second configuration. A knot capsule includes a body defining an internal knot cavity. The friction knot and a portion of the first loop are positioned within the internal knot cavity. The internal knot cavity defines one or more impingement surfaces configured to maintain the friction knot in a fixed position within the internal knot cavity when the friction knot is in the second configuration.

In some embodiments, the internal knot cavity of the knot capsule defines one or more push ledges. The push ledges can be configured to translate the friction knot on the first loop when the first loop is adjusted.

In some embodiments, a flat button is coupled to a distal end of the first loop. The flat button can include a torpedo button sized and configured for insertion through a bone tunnel.

In some embodiments, the friction knot is a prusik knot. The flexible strand can define a second loop. In some embodiments, a proximal portion of the knot capsule is sized and configured for partial insertion into a bone tunnel formed in a first bone. The first loop is sized and configured to extend through the bone tunnel from a first side of the first bone to a second side of the first bone.

In some embodiments, the body of the knot capsule defines a plurality of openings. Each of the plurality of openings receives one of the trailing end of a friction knot or a portion of the first flexible strand therethrough.

In various embodiments, a system is disclosed. The system includes a bone plate including a body having a bone contact surface and an opposing outer surface. The body defines at least one capsule hole extending from the outer surface to the bone contact surface. An anchor construct includes a flexible strand defining a first adjustable loop. A friction knot is coupled to a proximal end of the first adjustable loop. The friction knot is configured to allow adjustment of the first adjustable loop in a first configuration and is configured to prevent adjustment of the first adjustable loop in a second configuration. A knot capsule includes a body extending from a proximal end to a distal end and defining an internal knot cavity. The friction knot and a portion of the first adjustable loop are positioned within the internal knot cavity. The internal knot cavity defines one or more impingement surfaces configured to maintain the friction knot in a fixed position within the internal knot cavity when the friction knot is in the second configuration. A portion of the knot capsule is sized and configured to be inserted through the at least one capsule hole.

In some embodiments, the at least one capsule hole includes a countersink sized and configured to receive a proximal cap of the knot capsule therein. The bone contact surface of the bone plate can be contoured to conform to an outer surface of the first bone. The bone plate can define one or more screw holes extending from the outer surface to the bone contact surface.

In some embodiments, the bone anchor includes a flat button coupled to a distal end of the first adjustable loop. The flat button is sized and configured for insertion through the at least one capsule hole of the bone plate. The flat button can include a torpedo button.

In some embodiments, the internal knot cavity of the knot capsule defines one or more push ledges configured to translate the friction knot on the first adjustable loop when the first loop is adjusted.

In various embodiments, a method is disclosed. The method includes forming a bone tunnel through a first bone and a second bone. A portion of a bone anchor is inserted through the bone tunnel. The bone anchor includes a flexible strand defining a first adjustable loop, a friction knot coupled to a proximal end of the first adjustable loop, and a knot capsule having a body extending from a proximal end to a distal end and defining an internal knot cavity. The friction knot and a portion of the first adjustable loop are positioned within the internal knot cavity. A distal portion of the first adjustable loop is coupled to the second bone. The length of the first adjustable loop is shortened to reduce a distance between the first bone and the second bone. The friction knot is tightened to lock the first adjustable loop at a selected length. The internal knot cavity defines one or more impingement surfaces configured to maintain the friction knot in a fixed position within the internal knot cavity when the friction knot is in the second configuration.

In some embodiments, the distal portion of the at least one flexible loop is coupled to the outer surface of the second bone by a flat anchor button coupled to a distal end of the first adjustable loop. The anchor button can be inserted through the bone tunnel prior to coupling the distal portion of the flexible loop to the outer surface of the second bone.

In some embodiments, reducing the length of the first adjustable loop includes adjusting a position of the friction knot on the first adjustable loop. The internal knot cavity of the knot capsule defines one or more push ledges configured to translate the position of the friction knot on the first adjustable loop when the first adjustable loop is shortened.

In some embodiments, the method further includes positioning a bone plate against a medial surface of the first bone. The bone plate comprises a body having a bone contact surface and an opposing outer surface. The body defines at least one knot capsule opening extending from the outer surface to the bone contact surface. A portion of the knot capsule is inserted through the at least one knot capsule opening. Reducing the length of the first adjustable loop couples the bone plate to the first bone.

Although the subject matter has been described in terms of exemplary embodiments, it is not limited thereto. Rather, the appended claims should be construed broadly, to include other variants and embodiments, which may be made by those skilled in the art.

What is claimed is:

1. A bone anchor, comprising:
    a flexible strand defining a first adjustable loop;
    a friction knot coupled to a proximal end of the first adjustable loop, wherein the friction knot is configured to allow independent adjustment of the first adjustable loop in a first configuration and is configured to prevent any adjustment of the first adjustable loop in a second configuration; and
    a knot capsule having a body defining an internal knot cavity, wherein the friction knot and a portion of the first adjustable loop are positioned within the internal knot cavity, and wherein the internal knot cavity defines at least one impingement surface configured to maintain the friction knot in a fixed position within the internal knot cavity when the friction knot is in the second configuration after the friction knot is transitioned from the first configuration to the second configuration.

2. The system of claim 1, wherein the internal knot cavity of the knot capsule defines at least one push ledge.

3. The system of claim 2, wherein the at least one push ledge supports translation of the friction knot on the first loop when the first loop is adjusted.

4. The system of claim 1, further comprising a flat torpedo button coupled to a distal end of the first loop and sized for insertion through a bone tunnel.

5. The system of claim 1, wherein the friction knot is selected from the group consisting of: a prusik knot, a Klemheist knot, a Distel hitch, a Blake's hitch knot, a clove hitch knot, a Tennessee slider knot, and a Nice knot.

6. The system of claim 1, wherein the flexible strand defines a second loop and a proximal portion of the knot capsule is sized for partial insertion into a bone tunnel formed in a first bone, and wherein the first loop is sized to extend through the bone tunnel from a first side of the first bone to a second side of the first bone.

7. The system of claim 1, wherein the body of the knot capsule defines a plurality of openings, each of opening accepting at least one of the trailing end of a friction knot and a portion of the first flexible strand.

8. A system comprising:
    a plate comprising a body having a bone contact surface and an opposing outer surface, wherein the body defines at least one capsule hole extending from the outer surface to the bone contact surface; and
    an anchor construct comprising:
        a flexible strand defining a first independently adjustable loop;
        a friction knot coupled to a proximal end of the first independently adjustable loop, wherein the friction knot is configured to allow adjustment of the first independently adjustable loop in a first configuration and is configured to prevent any adjustment of the first independently adjustable loop in a second configuration; and
        a knot capsule having a body extending from a proximal end to a distal end and defining an internal knot cavity, wherein the friction knot and a portion of the first independently adjustable loop are positioned within the internal knot cavity, wherein the internal knot cavity defines at least one impingement surface maintain the friction knot in a fixed position within the internal knot cavity when the friction knot is in the second configuration after the friction knot is transitioned from the first configuration to the second configuration, and wherein a portion of the knot capsule is sized to be inserted through the at least one capsule hole.

9. The system of claim 8, wherein the at least one capsule hole includes a countersink sized to receive a proximal cap of the knot capsule.

10. The system of claim 8, wherein the bone contact surface of the plate is contoured to conform to an outer surface of the first bone and one or more screw holes communicate between the outer surface and the bone contact surface.

11. The system of claim 8, wherein the anchor construct further comprises a flat torpedo button coupled to a distal end of the first adjustable loop.

12. The system of claim 8, wherein the internal knot cavity of the knot capsule defines at least one push ledge configured to translate the friction knot on the first adjustable loop when the first loop is adjusted.

13. A bone anchor system, comprising:
a flexible strand defining a first adjustable loop;
a friction knot coupled to a proximal end of the first adjustable loop, wherein the friction knot is configured to allow independent adjustment of the first adjustable loop in a first configuration and is configured to prevent any adjustment of the first adjustable loop in a second configuration; and
a knot capsule having a body defining an internal knot cavity and including a plurality of edges that together define a D-shaped side loop opening at a distal end of the body, wherein the friction knot and a portion of the first adjustable loop are positioned within the internal knot cavity, and wherein the internal knot cavity defines at least one impingement surface configured to maintain the friction knot in a fixed position within the internal knot cavity when the friction knot is in the second configuration after the friction knot is transitioned from the first configuration to the second configuration.

14. The system of claim 13, wherein the D-shaped loop opening is sized and configured to allow a flexible strand defining one or more adjustable loops to pass through.

15. The system of claim 14, wherein each of the plurality of edges are smooth to allow for sliding of the flexible strand 4 during tightening and/or loosening of the adjustable loops.

16. The system of claim 13, wherein the at least one first impingement surface is positioned on a first side of the D-shaped loop opening and a second side of the D-shaped loop opening defines a second impingement surface.

17. The system of claim 13, wherein the impingement surfaces are configured to apply an impingement force to the friction knot.

18. The system of claim 13, wherein a proximal cap of the body defines the D-shaped opening sized and configured to receive at least one of an adjustment portion of the flexible strand and a locking strand extending from the friction knot.

19. The system of claim 13, wherein a first push ledge and a second push ledge are positioned on either side of the D-shaped opening configured to apply a push force that causes the friction knot to slide along the adjustable loops.

20. A system comprising:
a plate comprising a body having a bone contact surface and an opposing outer surface, wherein the body defines at least one capsule hole extending from the outer surface to the bone contact surface; and
an anchor construct comprising:
a flexible strand defining a first independently adjustable loop;
a friction knot coupled to a proximal end of the first independently adjustable loop, wherein the friction knot is configured to allow adjustment of the first independently adjustable loop in a first configuration and is configured to prevent any adjustment of the first independently adjustable loop in a second configuration; and
a knot capsule having a body extending from a proximal end to a distal end with a plurality of edges that together define a D-shaped side loop opening at a distal end of the body that communicates with an internal knot cavity, wherein the friction knot and a portion of the first independently adjustable loop are positioned within the internal knot cavity, wherein the internal knot cavity defines at least one impingement surface maintain the friction knot in a fixed position within the internal knot cavity when the friction knot is in the second configuration after the friction knot is transitioned from the first configuration to the second configuration, and wherein a portion of the knot capsule is sized to be inserted through the at least one capsule hole.

21. The system of claim 20, wherein the at least one capsule hole includes a countersink sized to receive a proximal cap of the knot capsule.

22. The system of claim 20, wherein the bone contact surface of the plate is contoured to conform to an outer surface of the first bone and one or more screw holes communicate between the outer surface and the bone contact surface.

23. The system of claim 20, wherein the anchor construct further comprises a flat torpedo button coupled to a distal end of the first adjustable loop.

24. The system of claim 20, wherein the internal knot cavity of the knot capsule defines at least one push ledge configured to translate the friction knot on the first adjustable loop when the first loop is adjusted.

25. The system of claim 20, wherein the D-shaped loop opening is sized and configured to allow a flexible strand defining one or more adjustable loops to pass through.

26. The system of claim 25, wherein each of the plurality of edges are smooth to allow for sliding of the flexible strand during tightening and/or loosening of the adjustable loops.

27. The system of claim 20, wherein the at least one first impingement surface is positioned on a first side of the D-shaped loop opening and a second side of the D-shaped loop opening defines a second impingement surface.

28. The system of claim 20, wherein the impingement surfaces are configured to apply an impingement force to the friction knot.

29. The system of claim 20, wherein a proximal cap of the body defines the D-shaped opening sized and configured to receive at least one of an adjustment portion of the flexible strand and a locking strand extending from the friction knot.

30. The system of claim 20, wherein a first push ledge and a second push ledge are positioned on either side of the D-shaped opening configured to apply a push force that causes the friction knot to slide along the adjustable loops.

* * * * *